US011653980B2

(12) United States Patent
Ando et al.

(10) Patent No.: US 11,653,980 B2
(45) Date of Patent: May 23, 2023

(54) SURGERY SUPPORTING APPARATUS CAPABLE OF MEASURING THE MOVEMENT OF A MEDICAL INSTRUMENT, CONTROL METHOD OF THE SAME, AND SURGERY SUPPORTING SYSTEM

(71) Applicant: A-Traction Inc., Kashiwa (JP)

(72) Inventors: Takehiro Ando, Kashiwa (JP); Hiroyuki Miyamoto, Kashiwa (JP); Keita Awano, Kashiwa (JP); Yoshihide Sugiura, Kashiwa (JP); Yuta Fukushima, Kashiwa (JP)

(73) Assignee: A-TRACTION INC., Kashiwa (JP)

( * ) Notice: Subject to any disclaimer, the term of this patent is extended or adjusted under 35 U.S.C. 154(b) by 826 days.

(21) Appl. No.: 16/574,315

(22) Filed: Sep. 18, 2019

(65) Prior Publication Data

US 2020/0093546 A1   Mar. 26, 2020

(30) Foreign Application Priority Data

Sep. 21, 2018   (JP) .............................. JP2018-178054

(51) Int. Cl.
*A61B 34/20* (2016.01)
*A61B 34/30* (2016.01)
(Continued)

(52) U.S. Cl.
CPC .............. *A61B 34/20* (2016.02); *A61B 17/29* (2013.01); *A61B 34/30* (2016.02); *A61B 90/08* (2016.02);
(Continued)

(58) Field of Classification Search
CPC ......... A61B 34/20; A61B 34/30; A61B 34/70; A61B 2034/2063; A61B 2034/2072; A61B 2090/062; A61B 2090/067; A61B 8/4272
See application file for complete search history.

(56) References Cited

U.S. PATENT DOCUMENTS

| 6,145,509 A | 11/2000 | Fanner |
| 7,841,980 B2 | 11/2010 | Minosawa et al. |

(Continued)

FOREIGN PATENT DOCUMENTS

| JP | S58071421 A | 4/1983 |
| JP | S61209382 A | 9/1986 |

(Continued)

OTHER PUBLICATIONS

Decision to Grant a Patent in Japanese Application No. 2018-178054 (machine translation 3 pages).
(Continued)

*Primary Examiner* — Anu Ramana
(74) *Attorney, Agent, or Firm* — Oliff PLC

(57) ABSTRACT

A surgery supporting apparatus capable of performing a manipulation using a surgical instrument to be inserted into a body cavity, comprises a measurement device configured to measure an insertion depth and an insertion angle, with respect to the body cavity, of a shaft of the surgical instrument inserted into the body cavity, as input of the manipulation, wherein the measurement device measures the insertion depth by measuring a sound wave propagating in a space between a transmitter attached to one of the surgical instrument and a position within a predetermined range from a position of insertion to the body cavity, and a receiver attached to the other.

15 Claims, 9 Drawing Sheets

(51) Int. Cl.
  *A61B 90/00* (2016.01)
  *A61B 17/29* (2006.01)
  *A61B 90/50* (2016.01)
  *A61B 1/313* (2006.01)
  *A61B 17/34* (2006.01)
  *A61B 17/00* (2006.01)

(52) U.S. Cl.
  CPC ......... *A61B 1/3132* (2013.01); *A61B 17/3421* (2013.01); *A61B 90/50* (2016.02); *A61B 2017/00398* (2013.01); *A61B 2017/2908* (2013.01); *A61B 2017/2927* (2013.01); *A61B 2034/2048* (2016.02); *A61B 2090/062* (2016.02); *A61B 2090/067* (2016.02); *A61B 2090/0811* (2016.02)

(56) References Cited

U.S. PATENT DOCUMENTS

| | | | |
|---|---|---|---|
| 8,000,926 B2* | 8/2011 | Roche | A61B 34/20 |
| | | | 702/159 |
| 9,974,621 B2 | 5/2018 | Inoue | |
| 10,758,209 B2* | 9/2020 | Boctor | A61B 5/0084 |
| 10,806,346 B2* | 10/2020 | Boctor | A61B 8/5207 |
| 11,096,656 B2* | 8/2021 | Vignon | A61B 8/0841 |
| 2002/0151767 A1 | 10/2002 | Sonnenschein et al. | |
| 2013/0172907 A1 | 7/2013 | Harris | |
| 2014/0000098 A1 | 1/2014 | Dunning et al. | |
| 2017/0020557 A1 | 1/2017 | Onuma | |
| 2017/0360520 A1 | 12/2017 | Hares | |
| 2018/0214167 A1* | 8/2018 | Overmyer | A61B 34/30 |

FOREIGN PATENT DOCUMENTS

| | | | |
|---|---|---|---|
| JP | 5-337127 A | 12/1993 | |
| JP | 10-272088 A | 10/1998 | |
| JP | 2001-275931 A | 10/2001 | |
| JP | 2007-301378 A | 11/2007 | |
| JP | 2015-24025 A | 2/2015 | |
| JP | 2016-131866 A | 7/2016 | |
| JP | 6149175 B1 | 6/2017 | |
| JP | 2018-110747 A | 7/2018 | |
| WO | WO-2017139556 A1* | 8/2017 | A61B 17/1703 |

OTHER PUBLICATIONS

Decision to Grant a Patent in Japanese Application No. 2019-004430 (machine translation 3 pages).
European Search Report dated Jan. 21, 2020, issued in counterpart EP application No. 19197967.3. (15 pages).
Office Action dated Jul. 19, 2022, issued in counterpart CN application No. 201910887540.9., with English translation. (15 pages).

* cited by examiner

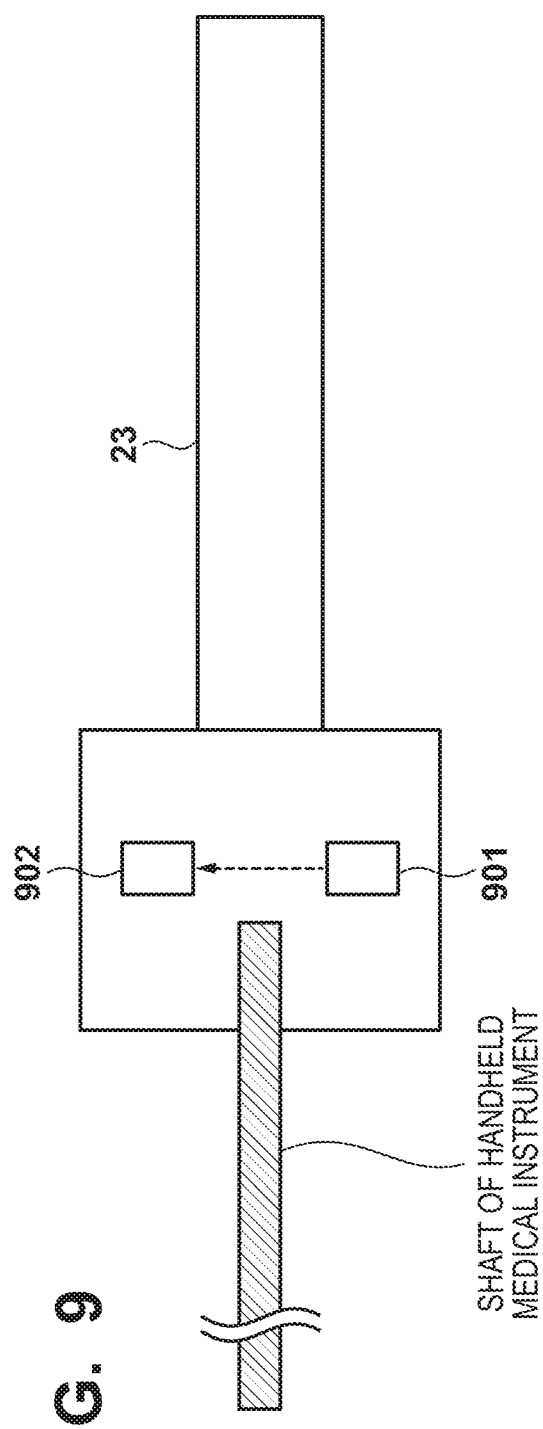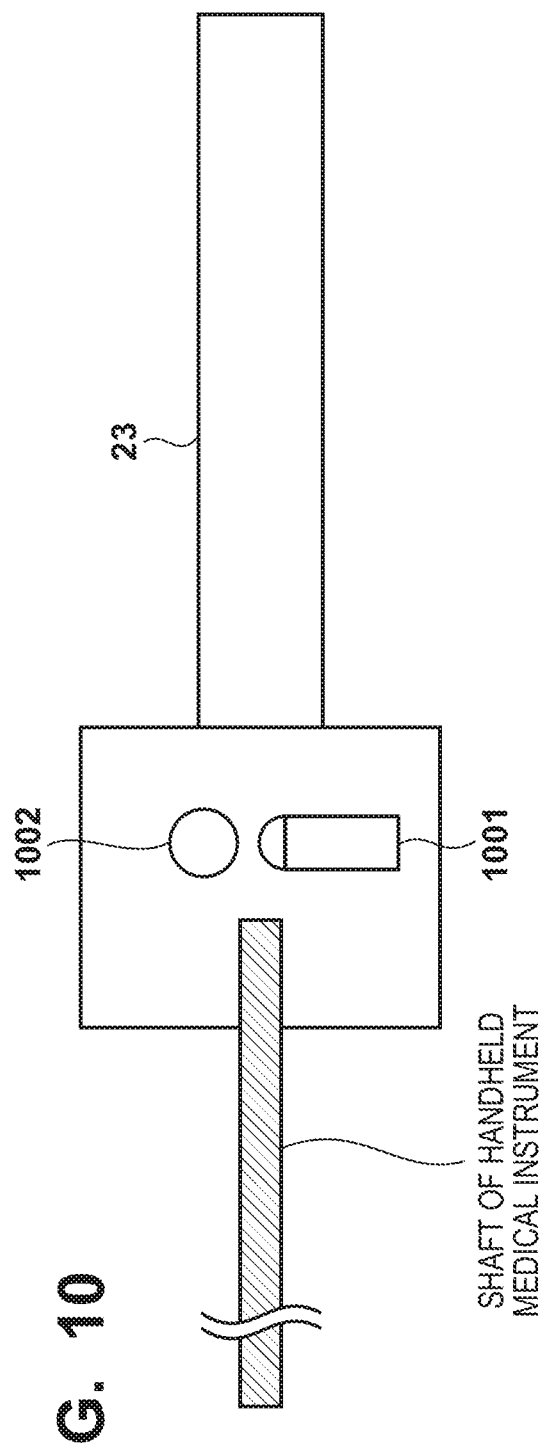

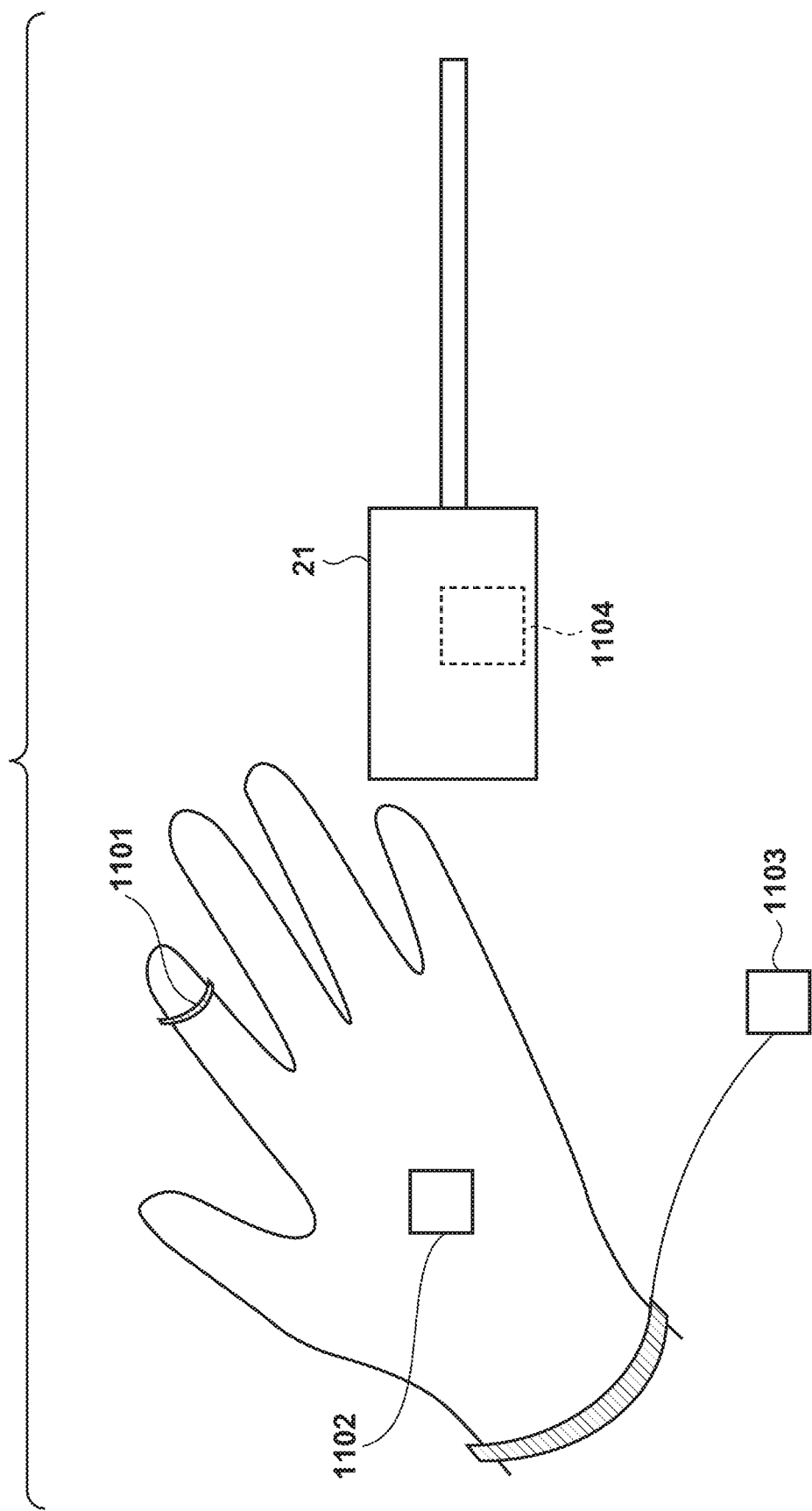

SURGERY SUPPORTING APPARATUS CAPABLE OF MEASURING THE MOVEMENT OF A MEDICAL INSTRUMENT, CONTROL METHOD OF THE SAME, AND SURGERY SUPPORTING SYSTEM

CROSS-REFERENCE TO RELATED APPLICATION

This application claims priority to and the benefit of Japanese Patent Application No. 2018-178054 filed on Sep. 21, 2018, the entire disclosure of which is incorporated herein by reference.

BACKGROUND OF THE INVENTION

Field of the Invention

The present invention relates to a surgery supporting apparatus capable of measuring the movement of a medical instrument, a control method of the same, and a surgery supporting system.

Description of the Related Art

A laparoscopic surgery by which a plurality of small-diameter holes are formed in the abdominal wall and an operator performs a surgery by inserting medical instruments such as a surgical instrument and an endoscope held in his or her hands into the body cavity through these holes is known. This laparoscopic surgery is generally performed such that a scopist who manipulates a laparoscope and an assistant who, for example, pulls an organ by a forceps assist an operator who performs a surgery by manipulating a plurality of surgical instruments such as an ultrasonic scalpel and a forceps. This sometimes complicates the laparoscopic surgery compared to an abdominal surgery performed by incising the abdomen. Accordingly, a technique of supporting an operator by a robot arm instead of support by the scopist and the like has been proposed (Japanese Patent Laid-Open Nos. 2015-24025 and 2007-301378).

Japanese Patent Laid-Open No. 2015-24025 has proposed a technique that measures a manipulation on a medical treatment instrument passed through a trocar by using an inclination angle detection sensor, a moving amount detection sensor, and a rotational amount detection sensor installed in the trocar, and performs control such that an end effector follows a following reference such as the distal end of the medical treatment instrument. Also, Japanese Patent Laid-Open No. 2007-301378 has proposed a technique that measures the posture of a surgical instrument by installing an inertia sensor such as an inclination sensor and an insertion amount sensor in a trocar, and controls the posture of a laparoscope so as to follow the distal end position of the surgical instrument.

In Japanese Patent Laid-Open No. 2015-24025, a roller that rotates in contact with the surface of a medical treatment instrument is used as the moving amount detection sensor for measuring the moving amount of a medical instrument in the major-axis direction. When measuring the moving amount of a medical treatment instrument by using the roller, however, a measurement error sometimes increases because the rotation in the contact state is influenced by, for example, the diameter and the surface material of the surgical instrument, and the attaching state of a substance. On the other hand, in Japanese Patent Laid-Open No. 2007-301378, an optical displacement sensor is used as the insertion amount sensor for measuring the movement of a medical instrument in the major-axis direction, and the insertion amount is measured based on a change in intensity of a semiconductor laser reflected on the surface of a surgical instrument. Even in this technique, however, a medical instrument is used to measure the intensity change of the laser beam, so a measurement error sometimes increases due to, for example, the surface material of the medical instrument and the state of a substance as an object.

SUMMARY OF THE INVENTION

The present disclosure has been made in consideration of the aforementioned issues, and realizes a technique capable of accurately measuring the movement in the major-axis direction of a medical instrument to be inserted into a body cavity.

In order to solve the aforementioned problems, one aspect of the present disclosure provides a surgery supporting apparatus capable of performing a manipulation using a surgical instrument to be inserted into a body cavity, comprising: a measurement device configured to measure an insertion depth and an insertion angle, with respect to the body cavity, of a shaft of the surgical instrument inserted into the body cavity, as input of the manipulation, wherein the measurement device measures the insertion depth by measuring a sound wave propagating in a space between a transmitter attached to one of the surgical instrument and a position within a predetermined range from a position of insertion to the body cavity, and a receiver attached to the other.

Another aspect of the present disclosure provides, a control method of a surgery supporting apparatus capable of performing a manipulation using a surgical instrument to be inserted into a body cavity, the surgery supporting apparatus including a measurement device, and the method comprising measuring an insertion depth and an insertion angle, with respect to the body cavity, of a shaft of the surgical instrument inserted into the body cavity, as input of the manipulation, wherein in the measuring, the insertion depth is measured by measuring a sound wave propagating in a space between a transmitter attached to one of the surgical instrument and a position within a predetermined range from a position of insertion to the body cavity, and a receiver attached to the other.

Still another aspect of the present disclosure provides, a surgery supporting system including a surgery supporting apparatus and a medical instrument driving apparatus, wherein the surgery supporting apparatus is a surgery supporting apparatus capable of performing a manipulation using a first surgical instrument to be inserted into a body cavity, and includes a measurement device configured to measure an insertion depth and an insertion angle, with respect to the body cavity, of a shaft of the first surgical instrument inserted into the body cavity, as input of the manipulation, the measurement device measures the insertion depth by measuring a sound wave propagating in a space between a transmitter attached to one of the first surgical instrument and a position within a predetermined range from a position of insertion to the body cavity, and a receiver attached to the other, and the medical instrument driving apparatus includes a driving device configured to control a posture of a second surgical instrument that is inserted into the body cavity and mechanically driven, in accordance with control information based on the insertion depth and the insertion angle measured by the measurement device of the surgery supporting apparatus.

Yet another aspect of the present disclosure provides, a surgery supporting apparatus that controls a posture of a first surgical instrument that is inserted into a body cavity from a first hole in an abdominal wall and mechanically driven, by using a second surgical instrument that is inserted into the body cavity from a second hole in the abdominal wall, comprising: a measurement device configured to measure an insertion depth, with respect to the body cavity, of a shaft of the second surgical instrument inserted into the second hole through a sheath tube; and a controller configured to output control information for controlling the posture of the first surgical instrument, based on at least the insertion depth measured by the measurement device, wherein the measurement device measures the insertion depth by measuring a sound wave propagating in a space between a transmitter attached to one of the sheath tube and the second surgical instrument, and a receiver attached to the other.

According to the present invention, it is possible to accurately measure the movement in the major-axis direction of a medical instrument to be inserted into a body cavity.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 9 is a view showing a configuration example (an example using light) for measuring an absolute distance according to the embodiment;

FIG. 10 is a view showing a configuration example (an example using a mechanical switch) for measuring an absolute distance according to the embodiment;

FIG. 11 is a view for explaining a tag for discriminating a handheld medical instrument and a configuration example of a tag detection sensor;

DESCRIPTION OF THE EMBODIMENTS

Exemplary embodiments of the present invention will be explained in detail below with reference to the accompanying drawings.

(Overall Configuration Example of Surgery Supporting System)

Figure 1:
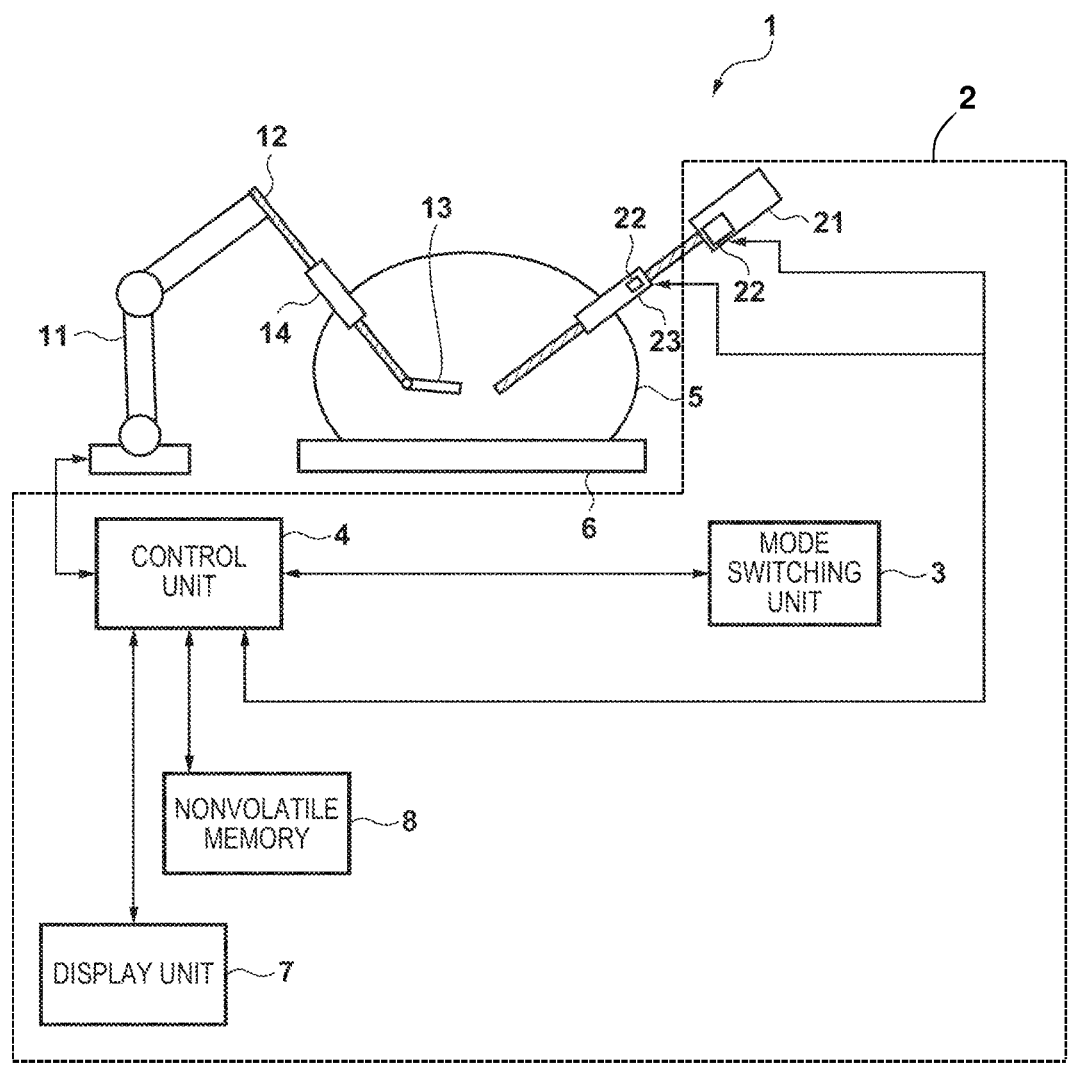
FIG. 1 is a view schematically showing an overall configuration example of a surgery supporting system.

First, an overall configuration example of a surgery supporting system 1 according to the present invention will be explained with reference to FIG. 1. FIG. 1 schematically shows a functional configuration example of the surgery supporting system 1 according to this embodiment. The surgery supporting system 1 according to this embodiment includes a surgery supporting apparatus 2 and a medical instrument driving unit 11 for controlling the posture of a surgical instrument or an end effector.

The surgery supporting apparatus 2 includes a position/posture measurement device 22 for measuring the posture of a surgical instrument (a handheld medical instrument 21) held by an operator, a mode switching unit 3 for switching control states, a control unit 4 for controlling coordinate conversion, a calculation of the position or the like of a control target, and the medical instrument driving unit 11, a display unit 7, and a nonvolatile memory 8. Note that a surgical instrument to be controlled by the medical instrument driving unit 11 will be called a robot medical instrument 12 in order to distinguish it from the handheld medical instrument 21.

FIG. 1 shows the way a surgical instrument and an end effector are inserted through sheath tubes into the body cavity of a patient lying on an operating table 6. The surgery supporting system 1 according to this embodiment is installed near an operator and a patient, and supports an operation performed by the operator by controlling the medical instrument driving unit 11 in cooperation with manipulation of a surgical instrument by the operator. The operator can alternately perform a medical treatment (for example, incision, excision, or suture of a part of an organ), and control of the robot medical instrument 12 or an end effector 13 (for example, pulling an organ by using a forceps), by manipulating the handheld medical instrument 21. The treatment using the handheld medical instrument 21 and the control of the robot medical instrument 12 or the end effector 13 can be switched by manipulating the mode switching unit 3.

Accordingly, unlike the control that always measures the distal end position of a surgical instrument to be used by an operator and causes a laparoscope or the like to follow the distal end position and its vicinity, the control of the robot medical instrument 12 according to this embodiment is performed in the interval of manipulation of the handheld medical instrument 21 for a medical treatment such as incision. Therefore, the measurement of the posture of the handheld medical instrument 21, which is performed to control the posture of the robot medical instrument 12 or the end effector 13, is completed within a relatively short time.

The medical instrument driving unit 11 includes a driving unit (for example, a robot arm) for controlling the movement of the robot medical instrument 12 and the posture of an end effector 13. For example, the driving unit can control the insertion angle of the robot medical instrument 12 to an abdominal wall 5, the movement (insertion depth) of the robot medical instrument 12 in the long-axis direction of a shaft, and the driving of the end effector 13. The mechanism of the driving unit can be, for example, a mechanism using an R guide, a mechanism using a parallel link, or a mechanism using a vertical multijoint arm, and the mechanism can have an arbitrary shape as long as the mechanism can actively control the posture of the end effector 13. The driving unit includes a plurality of positioning actuators such as servo motors, and current position information such as a joint angle of the mechanism can be obtained from an encoder included in each actuator. The medical instrument driving unit 11 is connected to the surgery supporting apparatus 2 via a communication path such as a LAN or a bus, and exchanges data with the control unit 4 of the surgery supporting apparatus 2. The medical instrument driving unit 11 can output current position information such as a joint angle obtained by an encoder to the control unit 4 of the surgery supporting apparatus 2. Also, the medical instrument driving unit 11 can control the movement of the robot medical instrument 12 and the posture of the end effector 13 based on control information output from the control unit 4. Note that in the following explanation, a simple term "robot" indicates all of the medical instrument driving unit 11, the robot medical instrument 12, and the end effector 13.

A part of the robot medical instrument 12 is inserted into the body cavity through a sheath tube 14 inserted into a small-diameter hole formed in the abdominal wall 5. For example, the robot medical instrument 12 and the end effector 13 include a forceps, a pair of tweezers, an electric scalpel, an aspiration tube, an ultrasonically activated scalpel, a hemostatic device, a radiofrequency ablation device, an endoscope, a thoracoscope, and a laparoscope, all of which are inserted into the body cavity and used. The robot medical instrument 12 and the end effector 13 can have a straight shape, and can also have a bending joint.

The handheld medical instrument 21 is a medical instrument which an operator actually moves with a hand to perform an ordinary treatment. The handheld medical instrument 21 is inserted into a body cavity through a sheath tube 23 inserted into a small-diameter hole formed in the abdominal wall 5, and capable of rotating around the intersection of the abdominal wall 5 and the sheath tube 23. A degree of freedom of a linear motion is added by inserting and removing the handheld medical instrument 21 through the sheath tube 23. That is, all degrees of freedom of the handheld medical instrument 21 can be measured if it is possible to measure a 3-degree-of-freedom motion of rotation and a 1-degree-of-freedom motion of a linear motion. The position/posture measurement device 22 is attached to the handheld medical instrument 21 and the sheath tube 23, and measures the position/posture of the handheld medical instrument 21 by using a sensor (to be described later). This sensor can be a general sensor capable of measuring a 6-degree-of-freedom absolute position/posture, and can also be a sensor for measuring a relative position/posture from a given time and a given position.

The position/posture measurement device 22 is configured by a combination of an inertia sensor capable of measuring a 3-degree-of-freedom posture, and a sound wave sensor capable of measuring the depth of insertion into a body cavity as a 1-degree-of-freedom linear motion. As the inertia sensor, it is possible to use, for example, a general sensor such as an acceleration sensor, an inclination sensor, a gyro sensor, or a magnetic field sensor, or a combination of these sensors. The handheld medical instrument 21 can be used as an input device when controlling the robot medical instrument 12 or manipulating a user interface displayed on the display unit 7.

The mode switching unit 3 includes a manipulation member for appropriately switching manipulation modes of the surgery supporting system. This manipulation member is a hand switch, a foot switch, or the like. The manipulation modes include a mode (to be also simply called a treatment mode) in which an operator actually performs a surgery by manipulating the handheld medical instrument 21 in order to perform a medical treatment, and a mode (to be also simply called a robot manipulation mode) in which the handheld medical instrument 21 is used to manipulate the robot medical instrument 12 or the end effector. When the operator switches the manipulation modes by using the mode switching unit 3, the control unit 4 switches the manipulation modes of the system in accordance with a signal from the mode switching unit 3, and records the current manipulation mode in a RAM (not shown). Note that it is also possible to obtain information such as a predetermined voice or a predetermined gesture via the mode switching unit 3, and cause the control unit 4 to perform switching to a manipulation mode corresponding to the input information.

The control unit 4 includes a central processing device such as a CPU or an MPU, a ROM, and a RAM, and controls the operation of each block of the surgery supporting apparatus 2 by executing a program stored in a storage medium such as the ROM or the nonvolatile memory 8. Also, the control unit 4 exchanges signals with the position/posture measurement device 22, and obtains the insertion angle and the insertion depth of the handheld medical instrument 21 manipulated by an operator, as will be described later. Furthermore, the control unit 4 obtains current position information such as joint angles (or displacement information between joint angles obtained based on the current position information) from encoders of the medical instrument driving unit 11. Based on the insertion angle and the insertion depth of the handheld medical instrument 21 with respect to the abdominal wall, the control unit 4 outputs, to the medical instrument driving unit 11, control information for controlling the movement of the robot medical instrument 12 or the posture of the end effector 13. Note that various methods can be used as a method of controlling the movement of the robot medical instrument 12 or the posture of the end effector 13 based on the insertion angle and the insertion depth of the handheld medical instrument 21. For example, a well-known method disclosed in Japanese Patent Laid-Open No. 2018-110747 can be used.

The display unit 7 includes a display device such as a liquid crystal display or an organic EL display, and displays a still image or a moving image of the body cavity captured by a laparoscope (not shown) inserted into the abdominal wall. The display unit 7 also displays, for example, the internal state (including, for example, numerical values indicating the postures of the robot and the handheld medical instrument 21) of the system, and a manipulation screen for manipulating this system. The display unit 7 may also be installed in a head mounted display which an operator wears.

The nonvolatile memory 8 includes a recording medium such as a semiconductor memory or a magnetic disk, and stores programs to be executed by the control unit 4, constants for operations, and the like.

(Configuration Example of Position/Posture Measurement Device)

Next, a configuration example of the position/posture measurement device 22 will be explained with reference to FIG. 2 by taking, as an example, a case in which the position/posture measurement device 22 is attached to the handheld medical instrument 21 and the sheath tube 23. In this example shown in FIG. 2, a sound wave transmitter 201 is attached to the sheath tube 23, and a sound wave receiver 202 is attached to the handheld medical instrument 21. The sound wave transmitter 201 and the sound wave receiver 202 are so arranged as to oppose each other. An inertia sensor 203 is also attached to the handheld medical instrument 21.

In the example of this embodiment, the sound wave transmitter 201 and the sound wave receiver 202 are, for example, elements capable of transmitting/receiving ultrasonic waves. However, they need not be ultrasonic devices, and measurement can also be performed by the same principle by using a pair of devices capable of transmitting/receiving sound waves such as a microphone and a speaker. Also, the inertia sensor 203 includes one or both of, for example, a gyro sensor and an acceleration sensor. The sound wave transmitter 201, the sound wave receiver 202, and the inertia sensor are connected to the control unit 4 by wireless connection or wired connection, and capable of exchanging measurement signals, control commands, and the like with each other. Based on a transmitted/received signal, the control unit 4 measures the distance (that is, the insertion depth of the handheld medical instrument 21 with respect to the sheath tube 23) between the sound wave transmitter 201 and the sound wave receiver 202 which oppose each other. Note that in this embodiment, an example in which the position/posture measurement device 22 transmits a measurement signal to the control unit 4 and the control unit 4 calculates the insertion depth will be explained. However, it is also possible to measure the insertion depth by only the position/posture measurement device 22. Also, in this embodiment, an example in which the position/posture measurement device 22 is attached to the handheld medical instrument 21 and the sheath tube 23 will be explained. However, it is also possible to further attach the position/posture measurement device 22 to the robot medical instrument 12 and a sheath tube 14, and measure the insertion depth of the robot medical instrument 12 with respect to the sheath tube 14.

Figure 2:
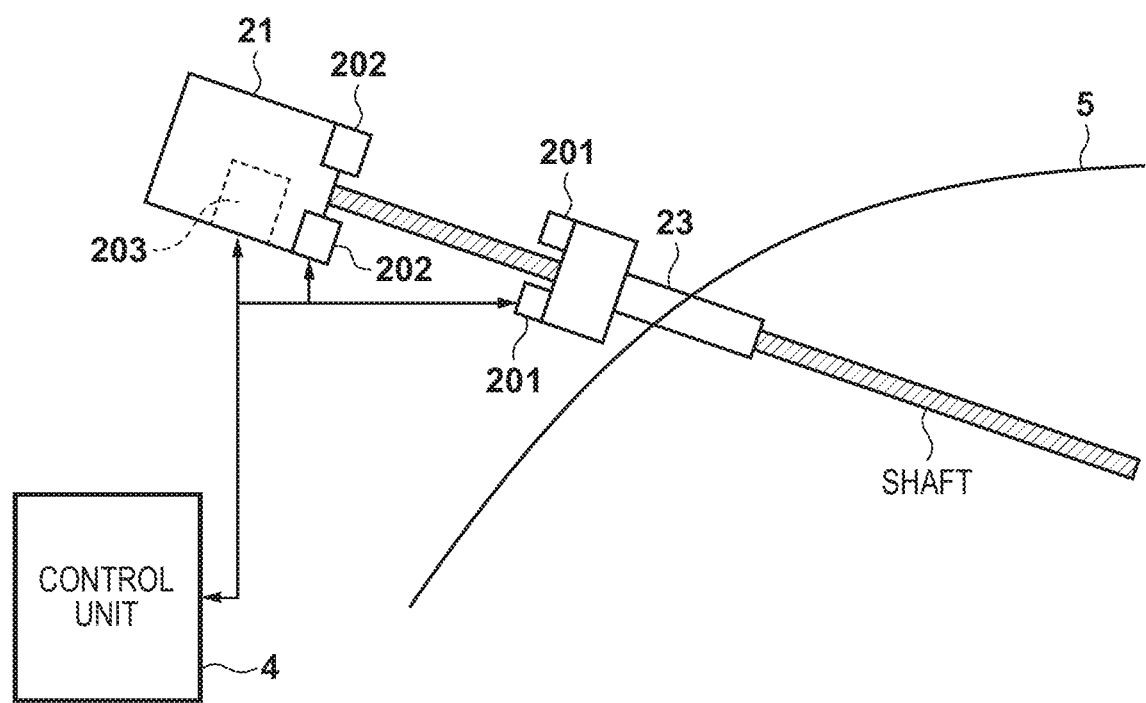
FIG. 2 is a view schematically showing a configuration example of a position/posture measurement device according to an embodiment.

In the arrangement shown in FIG. 2, the sound wave transmitter 201 is attached to the sheath tube 23, and the sound wave receiver 202 is attached to the medical instrument 21. However, it is also possible to attach the sound wave receiver 202 to the sheath tube 23, and the sound wave transmitter 201 to the medical instrument 21. In addition, the numbers of the sound wave transmitter 201 and the sound wave receiver 202 need not be one against one, and may also be multiple against multiple, as will be described later.

A sound wave propagates at a velocity of about 340 m/s in the air. Therefore, the distance between the sound wave transmitter and the sound wave receiver can be measured by measuring the time from transmission to reception. Note that it is generally desirable to be able to transmit and receive pulse sound waves in order to measure timings. In reality, however, it is difficult to transmit and receive pulse sound waves (due to, for example, the mechanical resonance frequency characteristics of the sound wave transmitter and the sound wave receiver). Generally, therefore, a sound wave having a few wavelengths to a few tens of wavelengths called a burst wave is used. When using the burst wave, the reception timing is determined by a threshold of the envelope of the burst wave. In this method, the distance can be obtained as an absolute value, but a time measurement error easily occurs due to the signal intensity. Consequently, it is sometimes impossible to obtain an accurate distance measurement result. Accordingly, the embodiment to be explained below uses a method of accurately measuring a relative distance by using the method of phase measurement.

(Arrangement of Control Unit for Distance Measurement)

Figure 3:
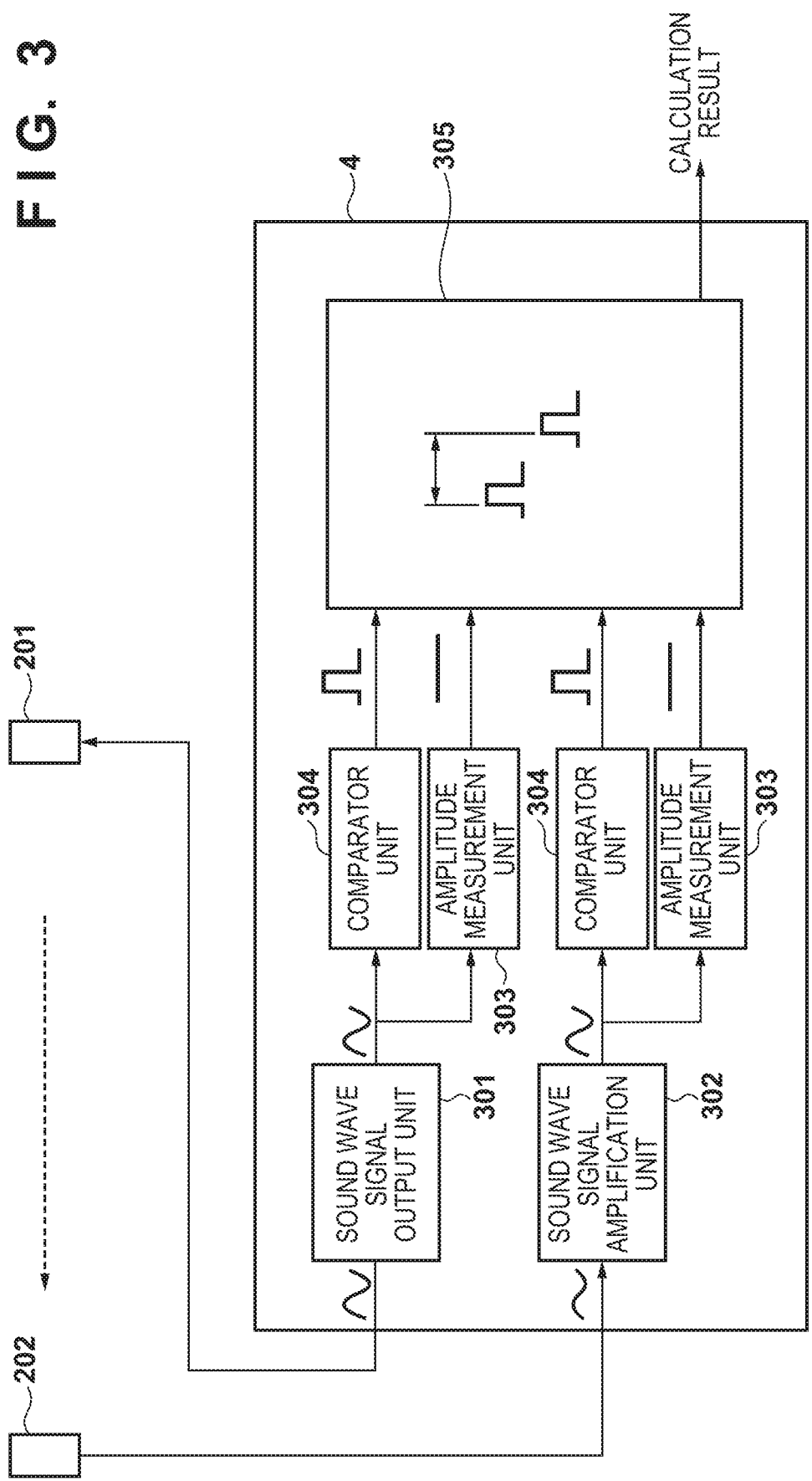
FIG. 3 is a view schematically showing a configuration example of a control unit for distance measurement according to the embodiment.

A configuration example of the control unit 4 for distance measurement will be explained below with reference to FIG. 3. The control unit 4 includes an arrangement for performing distance measurement by using a sound wave. FIG. 3 shows only this arrangement for performing distance measurement by using a sound wave, among the functions of the control unit 4.

The control unit 4 includes a sound wave signal output unit 301 for outputting a sound wave signal to the sound wave transmitter 201, a sound wave signal amplification unit 302 for performing amplification and noise filtering on a signal received by the sound wave receiver 202, an amplitude measurement unit 303, and a comparator unit 304. A signal transmitted from the sound wave signal output unit 301 and a signal received by the sound wave receiver 202 are input to the amplitude measurement unit 303 and the comparator unit 304.

The amplitude measurement unit 303 measures the amplitudes of the transmitted sound wave signal and the received sound wave signal. Note that a physical amount to be measured need not be the amplitude, and may also be an RMS (Root Mean Square) or a signal equivalent to the RMS and correlated with the amplitude. The comparator unit 304 converts the sound wave signal into a rectangular wave, thereby performing pre-processing for measuring the phase difference between transmission and reception. The comparator unit 304 outputs the sound wave signal converted into a rectangular wave to a calculation unit 305, and the calculation unit 305 measures the phase difference between transmission and reception. Note that the comparator unit 304 is used to simply perform phase difference measurement, and is not essential if the phase difference can be measured from the sound waveform. Note also that in FIG. 3, the control unit 4 includes the units 301 to 304, and they are arranged apart from the sound wave transmitter 201 and the sound wave receiver 202. However, the units 301 to 304 may also be arranged around the sound wave transmitter 201 or the sound wave receiver 202. Furthermore, some or all of the units 301 to 304 can be implemented by software to be executed by the control unit 4.

Note that although not shown in FIGS. 1 and 3, the control unit 4 can have an interface (that functions as a calculation result output unit) for outputting the result of a calculation performed by the calculation unit 305 to another apparatus. In addition, the control unit 4 can receive a signal output from the inertia sensor 203, and process the received signal and the sound wave signal at the same time by the calculation unit 305.

(Example of Distance Measurement Process)

Figure 4:
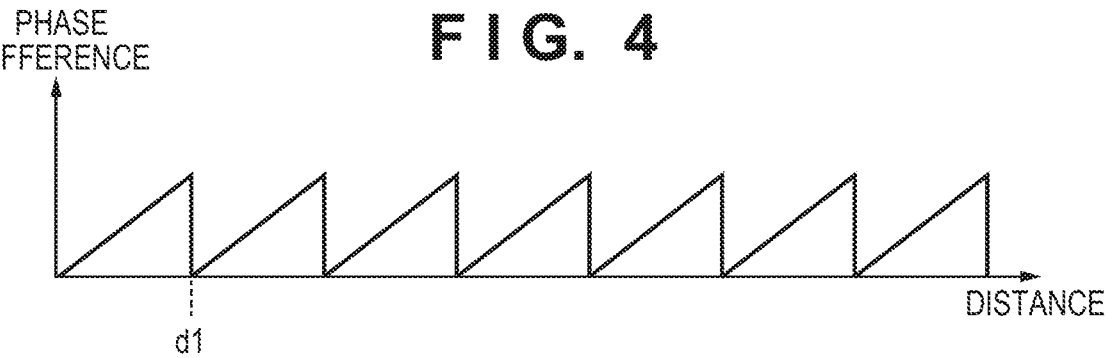
FIG. 4 is a graph showing the relationship between a distance between a sound wave transmitter and a sound wave receiver, and a phase difference according to the embodiment.

FIG. 4 is a graph showing the phase difference to be measured by the calculation unit 305 on the ordinate, and the distance between the sound wave transmitter 201 and the sound wave receiver 202 on the abscissa. As shown in FIG. 4, the relationship between the phase difference and the distance is represented by a waveform that periodically changes from 0° to 360°. If a target moves to a distance (dl) corresponding to one period, the distance can uniquely be calculated from the phase because the phase and the distance are proportional. However, a distance larger than dl cannot be determined because it is impossible to discriminate a period to which the phase corresponds.

Figure 5:
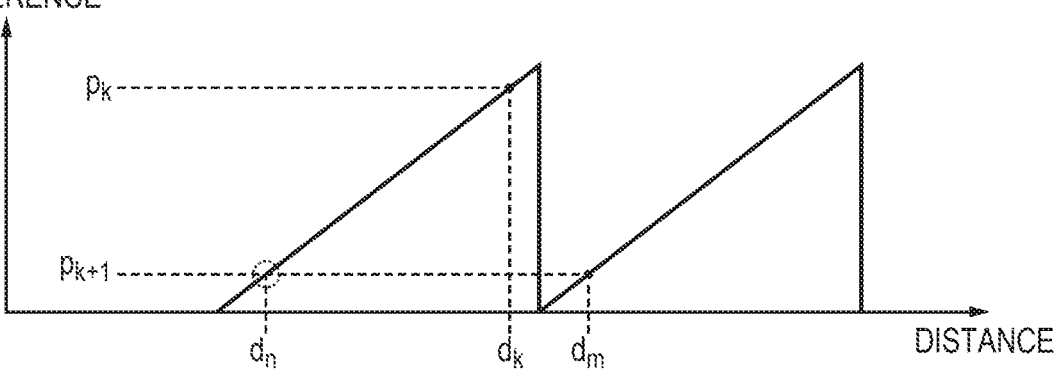
FIG. 5 is a graph for explaining a distance measurement process (a forward direction) according to the embodiment.

Accordingly, the calculation unit 305 successively calculates the changing amount of the phase, thereby performing conversion into an appropriate moving amount (that is, a distance changing amount) even when the movement occurs over different phases. Assume that the distance changes and the phase returns from 360° to 0° as shown in FIG. 5. In this case, values to be measured are a phase $p_k$ at time $t_k$, and a phase $p_{k+1}$ at time $t_{k+1}$. As described above, when focusing attention on only the value of the phase, two routes are possible from $p_k$ to $p_{k+1}$. When representing this by using a wavelength $\lambda$, position $d_n=\lambda(p_{k+1}-p_k)/360+d_k$, or $d_m=\lambda(p_{k+1}-p_k)/360+\lambda+d_k$. Therefore, a velocity constraint is set in order to determine an actual position.

When the phase changes from $p_k$ to $p_{k+1}$ from time $t_k$ to time $t_{k+1}$, the corresponding velocity is $(d_m-d_k)/(t_{k+1}-t_k)$ or $(d_n-d_k)/(t_{k+1}-t_k)$. When qualitatively representing this state, the distance decreases at a very high velocity or increases at a low velocity. In this case, this embodiment sets an assumption that the target does not move over a half wavelength during a given sampling interval. When representing a threshold according to this assumption by using the wavelength $\lambda$, $v_t=\lambda(t_{k+1}-t_k)/2$. In this case, in the example shown in FIG. 5, if the target has moved to the position $d_n$, the calculation unit 305 excludes this movement because the velocity exceeds the threshold (the target moves over the half wavelength during the sampling interval), and can determine that the target has moved to the position $d_m$ (at a velocity not exceeding the threshold).

Figure 6:
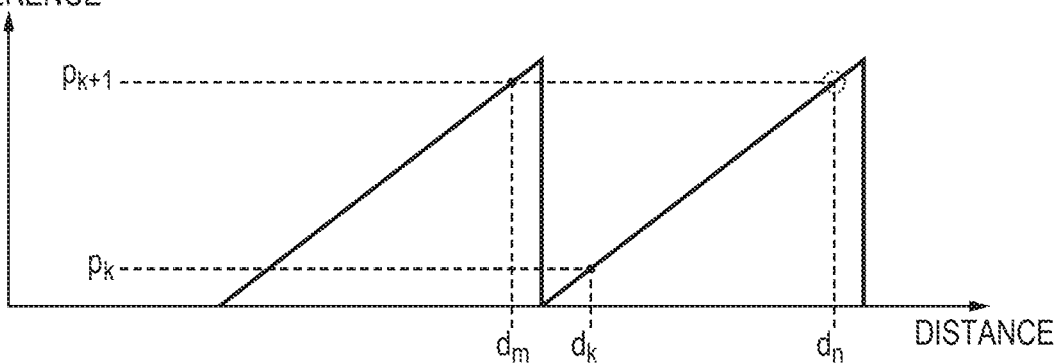
FIG. 6 is a graph for explaining a distance measurement process (an opposite direction) according to the embodiment.

In the example shown in FIG. 5, $p_{k+1}-p_k$ has a negative value. However, a similar procedure can be used even when this value is positive. FIG. 6 shows a state in which $p_{k+1}-p_k$ has a positive value. In this example shown in FIG. 6, the position obtained from the phase is $d_n=\lambda(p_{k+1}-p_k)/360+d_k$ or $d_m=\lambda(p_{k+1}-p_k)/360-\lambda+d_k$. Even in this example, the calculation unit 305 can determine the position to which the target has actually moved, by using the threshold of the velocity.

As described above, the calculation unit 305 can specify a relative moving amount by performing appropriate processing when the target moves over the phase change periods. This method does not require information on the amplitude of a sound wave signal. Therefore, the method has the advantage that the measurement result is not influenced at all even if the reception intensity changes due to the influence of disturbance of the surrounding environment.

The resolution of measurement is determined by the temporal resolution of phase difference measurement. This temporal resolution is generally equivalent to the clock frequency of a microcontroller or an FPGA. For example, when the phase difference is measured at a clock of 16 MHz, the resolution is about 0.02 mm. Also, when using a device such as an FPGA, the phase difference can be measured at the same period as that of the frequency of a sound wave, so a threshold $v_t$ of the velocity is half the sonic speed. This velocity is much higher than the velocity at which a human moves a target by holding it in a hand.

In this embodiment as described above, the insertion depth of the handheld medical instrument 21 is measured by measuring a sound wave propagating in the space between the sound wave transmitter 201 attached to one of the sheath tube 23 and the handheld medical instrument 21 and the sound wave receiver 202 attached to the other. More specifically, a sound wave is transmitted from the sound wave transmitter 201 attached to the sheath tube 23, and received by the sound wave receiver 202 attached to the handheld medical instrument 21, thereby measuring the insertion depth of the handheld medical instrument 21 in the linear motion direction based on the time of the sound wave propagating in the air. This makes it possible to largely reduce the influences of the surface material of the handheld medical instrument 21 and slight adhered substances when measuring the insertion depth. That is, it is possible to accurately measure the movement in the major-axis direction of a medical instrument to be inserted into a body cavity.

Also, in the above-described embodiment, the moving distance between the sound wave transmitter 201 arranged in the sheath tube 23 and the sound wave receiver 202 arranged in the handheld medical instrument 21 is measured based on the phase difference between a transmitted sound wave signal and a received sound wave signal. In this distance measurement based on the phase difference between sound wave signals, the relative moving amount of the handheld medical instrument 21 is determined by excluding the movement of the handheld medical instrument 21 at a velocity exceeding the predetermined threshold (a movement of a half wavelength or more during the sampling interval). Since the moving amount is measured by the phase difference, no information on the amplitude of a sound wave signal is necessary, so the moving amount can accurately be measured even when the reception intensity changes due to disturbance of the surrounding environment.

(Obstacle Detecting Process)

An example of performing an obstacle detecting process by using the above-described distance measurement process will be explained below. In this measurement method, the sound wave transmitter 201 and the sound wave receiver 202 are so arranged as to oppose each other, so no measurement can be performed if an obstacle exists between them. Therefore, several sound wave transmitters 201 and several sound wave receivers 202 are arranged around the shaft of the handheld medical instrument 21. This makes it possible to use a pair of the sound wave transmitter 201 and the sound wave receiver 202 having no obstacle in a sound wave path. The presence/absence of an obstacle can be determined from the value measured by the amplitude measurement unit 303 in the control unit 4. The amplitude of the measured signal increases or decreases depending on the distance as well. However, an amount that changes within the range of the length of the shaft of the handheld medical instrument 21 is clearly different from an amount that changes due to the presence/absence of an obstacle. Accordingly, an obstacle can be detected by presetting an appropriate threshold by an experiment or the like. Therefore, the control unit 4 determines whether there is an amplitude exceeding the threshold for obstacle detection, for each of a plurality of sound wave signals obtained from a plurality of pairs of the sound wave transmitters 201 and the sound wave receivers 202. Then, the control unit 4 selects a sound signal found to have an amplitude exceeding the obstacle detection threshold, as a sound signal not interrupted by an obstacle, and performs the distance measurement process by using the selected sound signal.

(Reduction of Influence of Rotation Around Shaft)

Generally, if a plurality of sound sources exist, sound waves interfere with each other, and a sound pressure distribution forms on the space. Even when a plurality of sound wave transmitters 201 are arranged in the sheath tube 23, the distance measurement process can be performed by using only one transmitter as the transmitting side in a given time width. By contrast, two or more receivers can be used on the receiving side. This embodiment uses this characteristic, and performs processing so as to decrease a distance measurement error with respect to a rotation around the shaft of the handheld medical instrument 21.

As shown in FIG. 2, for example, the sound wave transmitters 201 and the sound wave receivers 202 can be arranged around the shaft of the handheld medical instrument 21. In this case, when the handheld medical instrument 21 rotates around the shaft, the distance between the sound wave transmitter 201 and the sound wave receiver 202 corresponding to each other changes even at the same insertion depth.

Figure 7:
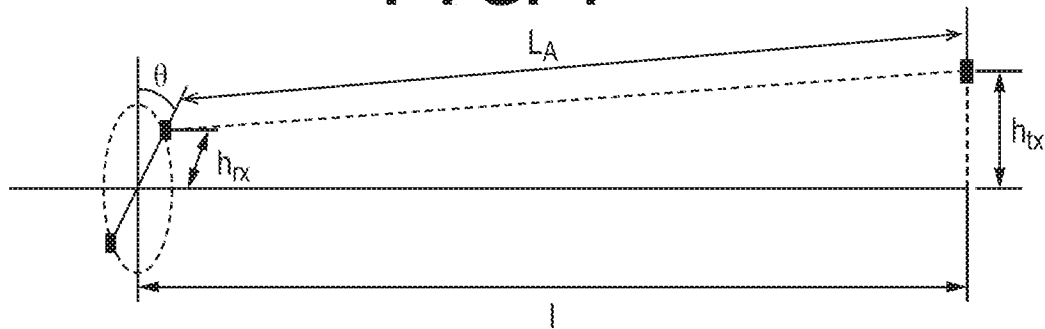
FIG. 7 is a graph for explaining processing when the sound wave receiver rotates around the shaft of a handheld medical instrument according to the embodiment.

The influence of a rotation around the shaft will be explained in more detail below with reference to FIG. 7. In an example shown in FIG. 7, sound wave receivers A and B as two sound wave receivers 202 are symmetrically attached at a distance of $h_{rx}$ so as to sandwich the shaft of the handheld medical instrument 21. In addition, the sound wave transmitters 201 are attached to the sheath tube 23 at a distance of $h_{tx}$ from the shaft. In this state, a distance $L_A$ between the sound wave transmitter 201 and the sound wave receiver A is represented by a distance 1 on the shaft and a rotational angle θ around the shaft as follows:

$$L_A = \sqrt{(h_{tx} - h_{rx}\cos\theta)^2 + (h_{rx}\sin\theta)^2 + l^2} \qquad (1)$$

Figure 8:
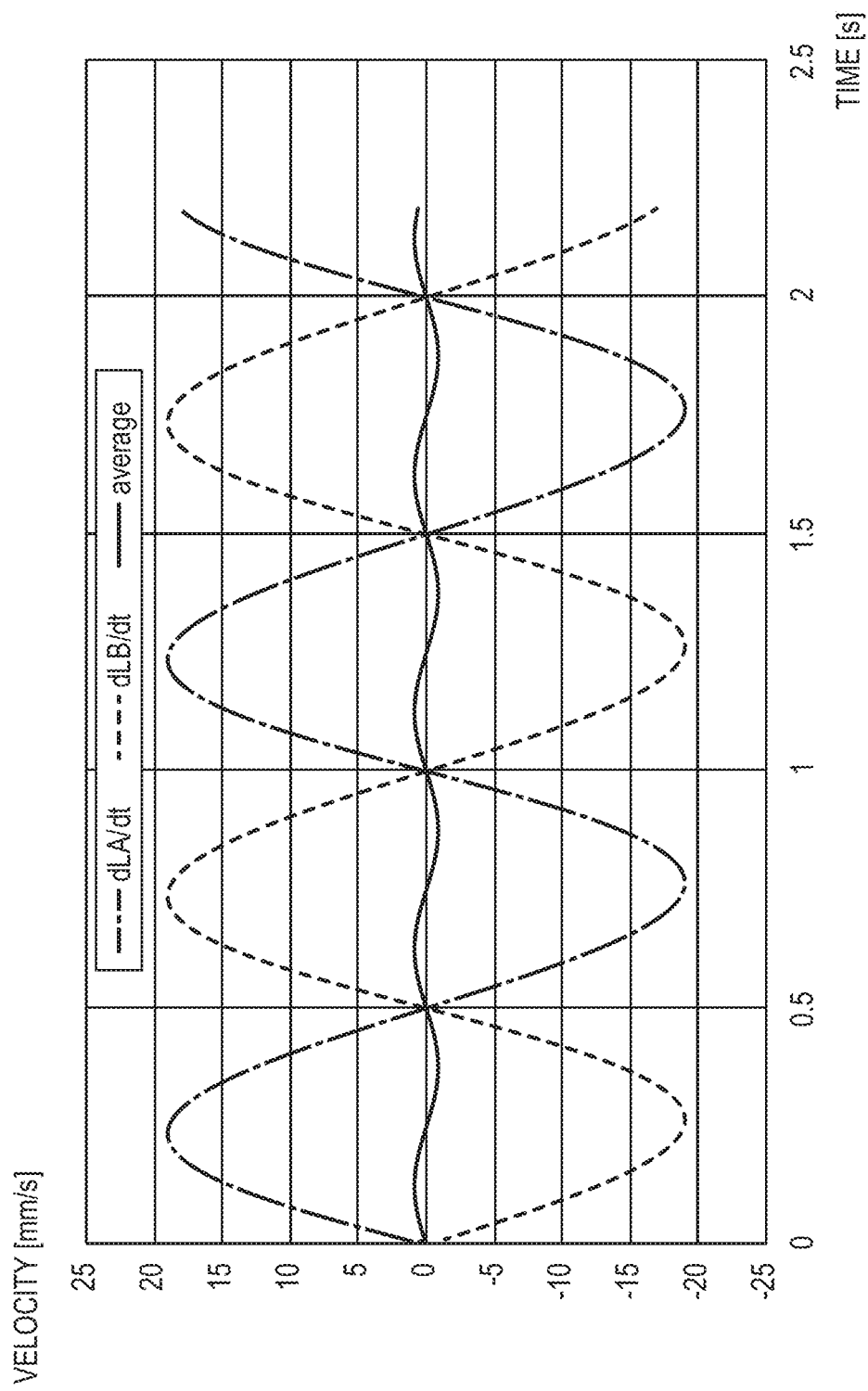
FIG. 8 is a graph for explaining an influence and its correction when the sound wave receiver rotates around the shaft of a handheld medical instrument according to the embodiment.

The position of the sound wave receiver B is equivalent to θ+180°. FIG. 8 shows a graph plotting the way θ changes at given 1. Referring to FIG. 8, the velocity of θ is 360°/s, and 1 is 100 mm. An absolute distance has no meaning due to the properties of measurement, so the ordinate represents the velocities of $L_A$ and $L_B$. Since 1 is fixed, the velocities of $L_A$ and $L_B$ are supposed to be 0. When the measurement value of each sound wave receiver is directly used, however, the velocities largely deviate from the actual velocity of 1 due to the change in θ. In this case, when measurement values such as a distance change (velocity) obtained from the sound wave signal of each receiver are added and the result is divided by 2 (that is, when leveling is performed by a plurality of measurement values), a result that is almost unaffected with respect to θ is obtained. As described above, when using a plurality of sound wave receivers, measurement values based on a plurality of sound wave receivers having, for example, a predetermined positional relationship are averaged. This makes it possible to cancel the influence of a rotation (that is, θ) around the shaft of the handheld medical instrument 21, and perform more accurate distance measurement.

In the example explained with reference to FIG. 7, a case in which the two sound wave receivers 202 are symmetrically attached with respect to the shaft of the handheld medical instrument 21 has been explained. However, when using three or more sound wave receivers 202 in this embodiment, the sound wave receivers 202 are arranged at equal angles around the shaft, and the measurement results are averaged in the same manner as when using two receivers. Consequently, the same result as described above can be obtained.

(Arrangement for Measuring Absolute Distance)

The distance measurement process explained so far measures a relative distance from the start of measurement. In this example, an arrangement that measures the distance between the sound wave transmitter and the sound wave receiver as an absolute distance will be explained.

As an arrangement for measuring the absolute distance according to this embodiment, the position/posture measurement device 22 includes, in the sheath tube 23, an insertion detection sensor (to be described later with reference to FIGS. 9 and 10) for detecting that the distal end of the shaft of the handheld medical instrument 21 has passed through the sheath tube 23. Note that in this embodiment, an insertion detection sensor using light (a photosensor) and an insertion detection sensor using a mechanical switch will be explained as examples of the insertion detection sensor. However, another method may also be used as long as a sensor can detect the insertion of the handheld medical instrument 21. As the other method, it is possible to use a method of measuring, for example, a change in inductance, a change in capacitance, or a change in pressure of a space through which the shaft passes.

FIG. 9 shows the insertion detection sensor using light. In this example, a light transmitter 901 and a light receiver 902 are attached to a portion through which the shaft of the handheld medical instrument 21 passes. Light emitted from the light transmitter 901 is intercepted when the shaft crosses. Accordingly, the insertion of the handheld medical instrument 21 can be detected in accordance with a change in light receiving state of the light receiver 902.

To convert the relative distance into the absolute distance, the control unit 4 causes the insertion detection sensor to detect the insertion of the shaft of the handheld medical instrument 21 into the sheath tube 23, and at the same time starts measuring the relative distance by using a sound wave (that is, clears the measurement value). Since the distance from the distal end of the medical instrument to the sound wave receiver 202 is known, conversion to the absolute distance from the insertion detection sensor as an origin is possible. Note that the position of the insertion detection sensor as an origin can be determined by, for example, specifying the absolute position of the rotation center of the sheath tube 23 in advance, and obtaining the distance from the rotation center to the detection position and the angle of the sheath tube 23.

In the example shown in FIG. 9, the light transmitter 901 and the light receiver 902 exist inside the sheath tube 23. However, if the material of the sheath tube 23 transmits light, the light transmitter 901 and the light receiver 902 may also be attached to the outside of the sheath tube 23 so as to be detachable. To prevent a reaction even when a biological tissue such as blood adheres, a near infrared region can be used as the wavelength of light.

FIG. 10 shows another example of the insertion detection sensor using a mechanical switch. This example has a mechanism in which a switch 1001 is pressed when the shaft of the handheld medical instrument 21 passes through the sheath tube 23. Also, detection errors can be reduced by forming, in addition to the switch, a guide roller 1002 for receiving a counterforce, on the side opposite to the switch. The guide roller 1002 does not necessarily rotate, and may also be a small projection if the friction is small. In addition, the switch 1001 is not limited to a general mechanical switch, and may also be a device that is turned on and off when the movement or deformation of an object is detected. For example, it is possible to use a hole sensor, a photosensor, an inductance sensor, or a capacitance sensor.

(Another Arrangement for Measuring Absolute Distance)

The absolute position can also be obtained by using another arrangement without using the insertion detection sensor for the shaft of the handheld medical instrument 21. For example, an arrangement that intermittently transmits a sound wave can be used as the arrangement for measuring the absolute distance. When using an intermittent sound wave, the absolute distance based on the arrival time of the sound wave can be measured by detecting the leading edge or the trailing edge of a received signal when the transmission of the sound wave is started or stopped. Note that the leading edge or the trailing edge of the received signal can be detected in the same manner as in the measurement method using a burst wave described earlier with reference to FIG. 2. That is, the reception timing is determined based on the threshold of the envelope of the burst wave. By thus obtaining the absolute distance based on the arrival time of the sound wave, the absolute distance between the sound wave transmitter and the sound wave receiver can always be measured by the accurate relative position measurement described above.

(Arrangement for Automatically Discriminating Exchanged Handheld Medical Instrument)

In the above-described arrangement, an example in which the sheath tube 23 and the handheld medical instrument are used in one-to-one correspondence has been explained. In an actual surgery, however, a medical instrument to be used is selected from a plurality of medical instruments, thereby switching medical instruments to be inserted into one sheath tube 23.

When executing measurement for the handheld medical instrument 21 to be inserted anew into the sheath tube 23, it takes time to remove the sensor attached to the handheld medical instrument 21 that is used (before being exchanged), and attach the removed sensor to the handheld medical instrument 21 that is to be used (after being exchanged). Therefore, the sound wave receiver 202 is attached beforehand to each of a plurality of handheld medical instruments 21, and the control unit 4 switches sensor data as a processing target (when the handheld medical instruments 21 are exchanged). This does not disturb the progress of a surgery, and facilitates the manipulation of the surgery supporting system.

Especially when preventing disturbance of the progress of a surgery, it may be beneficial if the system is able to automatically discriminate switching of the handheld medical instruments 21, instead of manually switching the handheld medical instruments 21 by an operator by using a switch or the like. Therefore, an arrangement for automatically discriminating a sensor of the handheld medical instrument 21 to be used will be explained with reference to FIGS. 11 and 12. Note that a sensor (that is, the position/posture measurement device 22) attached to each of a plurality of handheld medical instruments 21 is connected to the control unit 4 by wired connection or wireless connection.

As a method of discriminating a surgical instrument currently being used, as shown in FIG. 11, detachable tags 1101 to 1103 are attached to the hand of an operator, and an approach or contact of the tag is detected by using a tag detection sensor 1104 of the handheld medical instrument 21. For example, a tag made of a magnet is attached to the hand of an operator, and detected by a tag detection sensor formed by a magnet sensor. When receiving a detection signal indicating detection of the tag from the tag detection sensor, the control unit 4 discriminates a handheld medical instrument to which the tag detection sensor having detected the tag is attached, as a handheld medical instrument to be used.

When transmitting a detection signal to the control unit 4, the tag detection sensor 1104 can also transmit an ID (a tag detection sensor ID) for identifying the tag detection sensor 1104. Upon receiving the tag detection sensor ID and the detection signal from the tag detection sensor 1104, the control unit 4 specifies the handheld medical instrument 21 currently being used based on the ID, and obtains information of the handheld medical instrument 21. This information of the handheld medical instrument 21 contains, for example, medical instrument information such as the type of the medical instrument and the length of the shaft of the medical instrument, and other information such as the number of attached sound wave receivers, the angles between the sound wave receivers, and the distances from the shaft. For example, a table associating the information of a handheld medical instrument to which the tag detection sensor 1104 is attached with the tag detection sensor ID is stored in the nonvolatile memory 8 in advance. When the tag detection sensor 1104 detects the tag, therefore, the control unit 4 can obtain, from the table, the information of the handheld medical instrument to which the tag detection sensor is attached. Then, the control unit 4 can switch distance measurement processes in accordance with the number of sound wave receivers, or adjust control information in accordance with the characteristics of the handheld medical instrument 21. When the tag detection sensor 1104 detects the tag, the control unit 4 can also display, on the display unit 7, at least one of the detection of the handheld medical instrument 21 currently being used, and information indicating the type and characteristics of the detected handheld medical instrument. Consequently, an operator can grasp that the system has recognized the exchange of the handheld medical instruments, and can grasp information of the handheld medical instrument recognized by the system.

The positions and forms of attaching tags to an operator can be different as shown in FIG. 11. Also, the attaching position and attaching form of a tag can be changed in accordance with the shape of the handheld medical instrument 21. For example, the tag 1101 can be attached to the fingertip, the tag 1102 is attached to the palm of the hand, and the tag 1103 is embedded in a strap extending from the wrist. When using any of these tags, the tag can easily approach the tag detection sensor of the handheld medical instrument 21 when an operator uses the handheld medical instrument 21. Also, each of the tag and the tag detection sensor need not be one, and they can be attached to several portions so that all surgical instruments can be used. The tag detection sensor is not limited to a magnetic force sensor, and another method can also be used as long as the method can determine an approach of the tag. For example, a method using near field communication such as RFID can be used.

When a handheld medical instrument approaching the hand of an operator is automatically selected as a handheld medical instrument to be used as described above, the system can also be used for the purpose of canceling a manipulation if the operator has dropped the handheld medical instrument from the hand. In this case, if the handheld medical instrument 21 leaves the hand of the operator, the tag cannot be recognized any longer. In accordance with this change in identification state of the tag, therefore, the control unit 4 can handle the handheld medical instrument 21 as it is not used (for example, can ignore the signal from the position/posture measurement device 22).

(Selection of Handheld Medical Instrument by Sound Wave)

Figure 12:
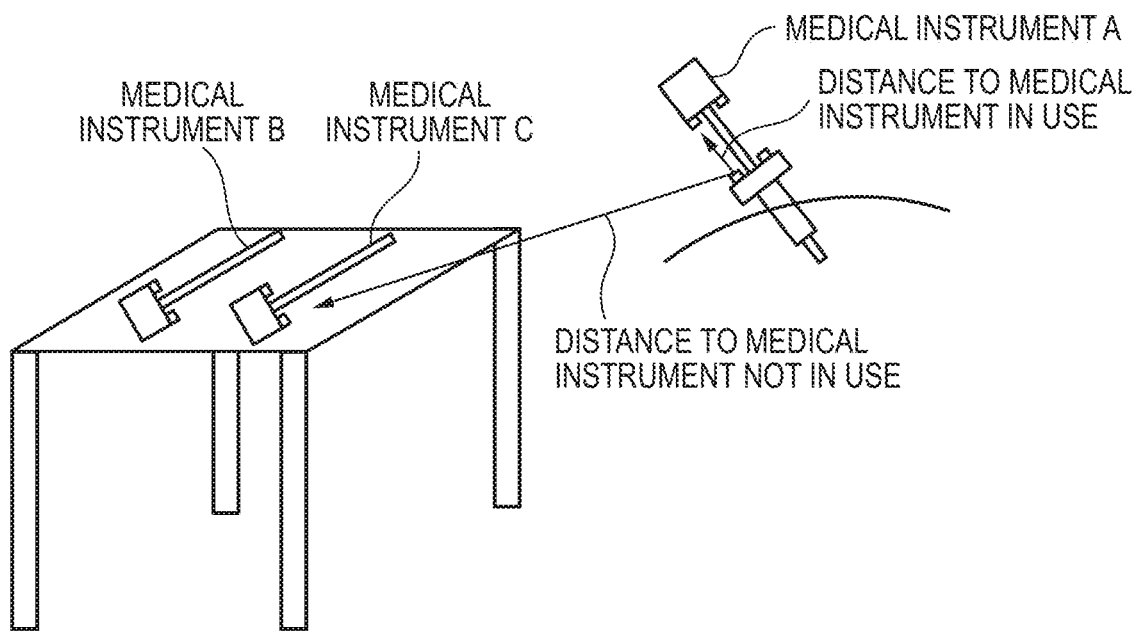
FIG. 12 is a view for explaining a processing example (an example using a detection distance) for discriminating a plurality of handheld medical instruments.

It is also possible to identify the handheld medical instrument 21 currently being used by using a sound wave. As shown in FIG. 12, medical instruments A to C as the handheld medical instruments 21 exist. In this example shown in FIG. 12, an operator is using the medical instrument A, and the other medical instruments are placed on a machine table in a place spaced apart to some extent from the sheath tube 23 (that is, a place exceeding a measurable distance).

In this state, the amplitude of a sound wave measured by each sound wave receiver 202 is measured. When a medical instrument is placed on the machine table, the medical instrument is normally at a distance at which almost no sound wave can be measured, so the amplitude of a sound wave becomes smaller than a predetermined threshold. Therefore, if the amplitude of a measured sound wave is equal to or larger than the predetermined threshold, the control unit 4 can determine that the corresponding handheld medical instrument 21 is currently being used.

In the above example, it is assumed that a medical instrument that is not in use is placed at a distance at which no sound wave can be measured. However, there is still a possibility that a medical instrument that is not in use is placed in a position where a sound wave is measurable. In this embodiment, therefore, in order to select a handheld medical instrument more accurately, an absolute distance is measured by using a burst wave, in addition to the above-mentioned amplitude. Generally, the lengths of surgical instruments to be used in a laparoscopic surgery are almost constant. Accordingly, even when a medical instrument that is not in use exists in a position where a sound wave is measurable, the control unit 4 determines that the medical instrument is not in use, if the distance from the sound wave transmitter 201 is equal to or larger than the length of a general medical instrument (that is, a predetermined length threshold).

Figure 13:
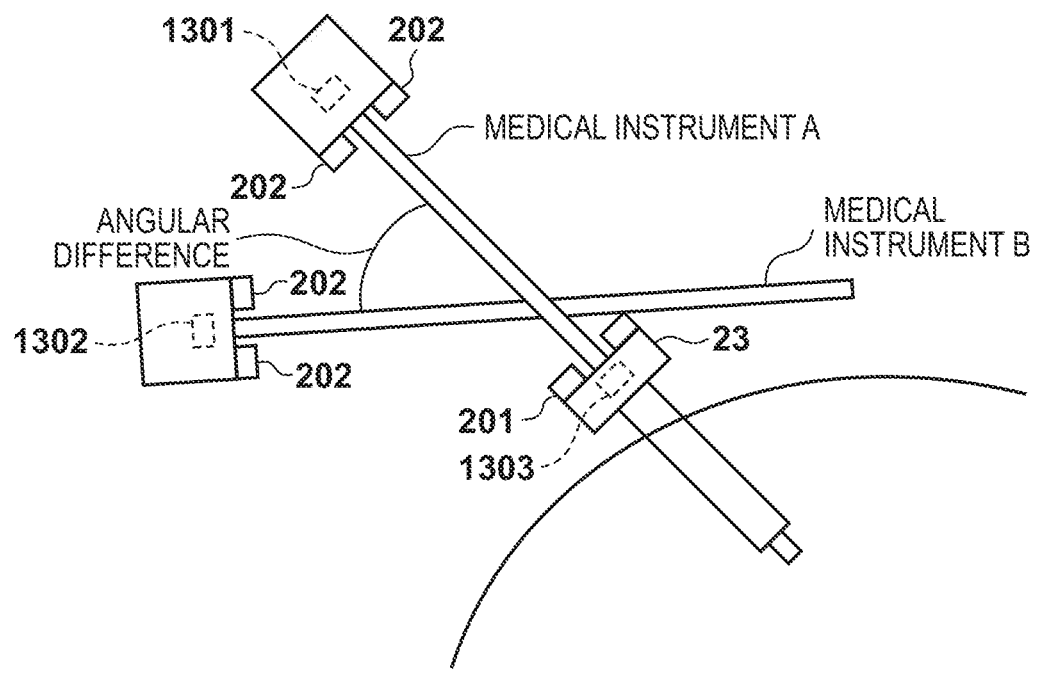
FIG. 13 is a view for explaining a processing example (an example using inertia sensors) for discriminating a plurality of handheld medical instruments.

Furthermore, a discrimination process further using an inertia sensor can also be performed by taking account of a case in which a medical instrument that is not in use is placed at a distance shorter than the length of a general medical instrument from the sound wave transmitter 201. As shown in FIG. 13, this embodiment uses inertia sensors 1301 and 1302 as the inertia sensors 203 attached to the handheld medical instrument 21, and a sheath-tube-side inertia sensor 1303 attached to the sheath tube 23.

Since the medical instrument A as the handheld medical instrument 21 currently being used is inserted into the sheath tube 23, postures obtained from the inertia sensors of the handheld medical instrument 21 and the sheath tube 23 are supposed to match. On the other hand, the posture of the medical instrument B that is placed near the sheath tube 23 but is not in use is almost not parallel to the posture of the sheath tube 23. That is, the control unit 4 can discriminate a handheld medical instrument currently being used based on the angular difference of the posture of each medical instrument. In practice, there is a gap between the sheath tube and the shaft of the medical instrument, so they are not completely parallel. In addition, only a relative value can be measured for a rotation around the gravity axis, so no comparison is possible. Accordingly, the control unit 4 can discriminate an inserted handheld medical instrument when, for example, an inclination to the gravity axis of the sheath tube 23 and an inclination to the gravity axis of the handheld medical instrument 21 match to some extent (that is, when the angular difference is smaller than a predetermined threshold).

(Configuration of Detachable Sensor Unit)

Figure 14:
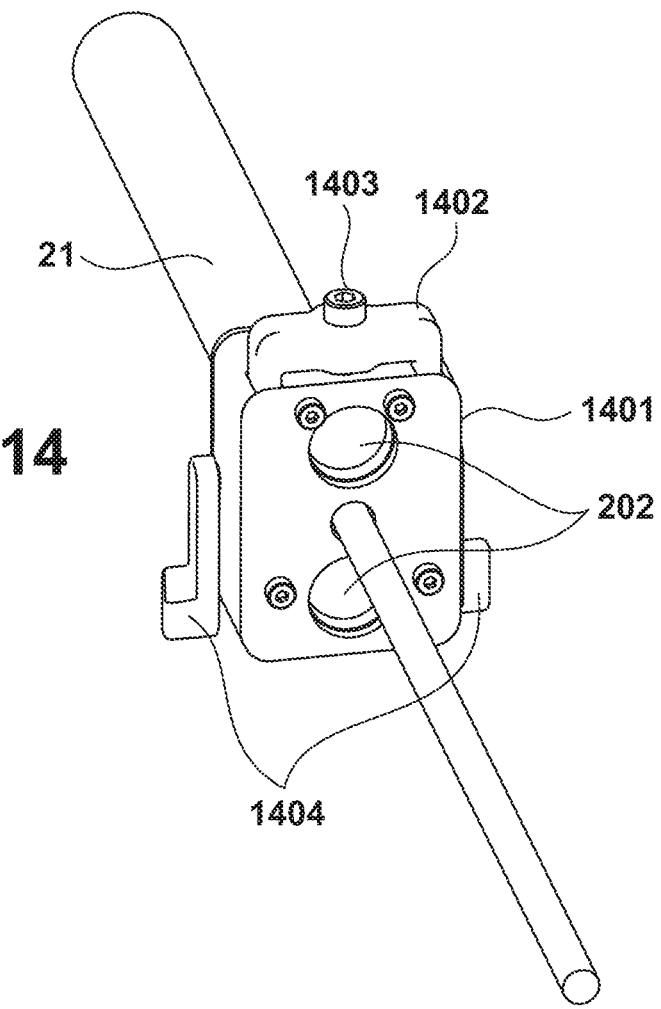
FIG. 14 is a view schematically showing a configuration example of a sensor unit including sound wave receivers and an inertia sensor according to the embodiment.

The sound wave receiver 202 and the inertia sensor 203 can be incorporated into the handheld medical instrument 21, but it is often convenient if they are detachable in order to use various kinds of medical instruments. FIG. 14 shows a configuration example of a sensor unit 1401 including the sound wave receiver 202 and the inertia sensor 203 according to this embodiment. The sensor unit 1401 is configured as a housing detachable from the handheld medical instrument 21. The sensor unit 1401 is fixed to the shaft of the handheld medical instrument 21 by fastening a screw 1403 of a fixing tool 1402.

The sensor unit 1401 may also be attached directly to the handle of the handheld medical instrument 21, instead of the shaft, depending on the shape of the handheld medical instrument 21. Also, as shown in FIG. 14, the sensor unit 1401 can include levers 1404 for performing switching, in addition to the sound wave receiver 202 and the inertia sensor 203. In this case, an operator can perform switching while holding the handheld medical instrument 21. The levers 1404 exist on the left and right sides in the example shown in FIG. 14, but their positions do not matter.

Figure 15:
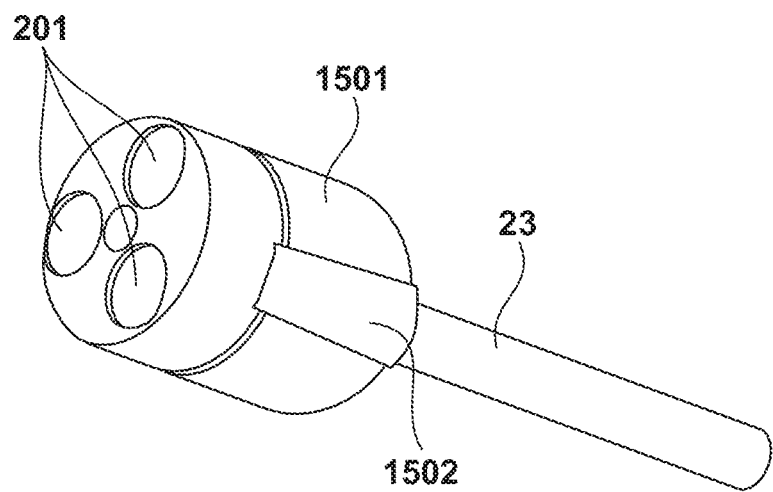
FIG. 15 is a view schematically showing a configuration example when a sensor unit including sound wave transmitters is attached to a sheath tube according to the embodiment.

It is also convenient if a sensor unit 1501 including the sound wave transmitter 201 is attached to the sheath tube 23 so as to be detachable. FIG. 15 shows a configuration example when the sensor unit 1501 including the sound wave transmitter 201 is attached to the sheath tube 23. In this example, the sensor unit 1501 forms a housing detachable from the sheath tube 23, and includes three sound wave transmitters 201. Also, the sensor unit 1501 is fixed to the sheath tube 23 by a fixing tool 1502. A hole for passing the shaft of the handheld medical instrument 21 is formed in the center of the sensor unit 1501.

Note that this embodiment has been explained by taking, as an example, the case in which the position and posture of the handheld medical instrument 21 are measured by installing the position/posture measurement devices 22 in the handheld medical instrument 21 and the sheath tube 23. However, it is also possible to measure the position and posture of the robot medical instrument 12 by attaching the position/posture measurement devices 22 of this embodiment to the robot medical instrument 12 and the sheath tube 14. That is, the position/posture measurement device 22 can also be used as a sensor for controlling the motion of the robot medical instrument 12, and can be used instead of an encoder of the joint portion of the medical instrument driving unit 11.

(Other Embodiments)

Furthermore, the individual units of the above-described surgery supporting system can be implemented as they are separated or integrated. Also, in addition to a case in which the control unit reads out a program of a computer for executing the above-described processing from a recording medium and executes the readout program, the present invention can include a case in which the control unit obtains the program by wired communication or wireless communication and executes the obtained program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A surgery supporting apparatus for performing a manipulation using a first surgical instrument configured to be inserted into a body cavity through a sheath tube configured to be inserted into the body cavity at an insertion position, the apparatus comprising:
 a measurement device configured to measure an insertion depth and an insertion angle, with respect to the body cavity, of a shaft of the first surgical instrument,
 wherein the measurement device includes a transmitter that is configured to be attached to one of the first surgical instrument and the sheath tube, and a receiver that is configured to be attached to the other of the first surgical instrument and the sheath tube,
 the measurement device measures the insertion depth by measuring a sound wave propagating in a space between the transmitter and the receiver, and the manipulation is performed based on the insertion depth and the insertion angle measured by the measurement device.

2. The surgery supporting apparatus according to claim 1, wherein the measurement device measures the insertion depth based on a phase difference between a sound wave signal transmitted from the transmitter and a sound wave signal received by the receiver.

3. The surgery supporting apparatus according to claim 1, wherein in order to measure the insertion depth, the measurement device measures a change amount of a distance between the transmitter and the receiver, based on a phase difference between a sound wave signal transmitted from the transmitter and a sound wave signal received by the receiver.

4. The surgery supporting apparatus according to claim 3, wherein in the measurement based on the phase difference, the measurement device measures the change amount of the distance between the transmitter and the receiver by excluding a movement of the first surgical instrument at a velocity exceeding a predetermined threshold.

5. The surgery supporting apparatus according to claim 1, wherein the receiver includes a plurality of receivers arranged at a predetermined angle around the shaft of the first surgical instrument, and
the measurement device measures the insertion depth by receiving a sound wave transmitted from one transmitter by the plurality of receivers, and leveling measurement values based on sound wave signals received by the plurality of receivers.

6. The surgery supporting apparatus according to claim 1, wherein the measurement device further includes an insertion detection sensor configured to detect that a distal end of the shaft of the first surgical instrument has passed through the sheath tube inserted into the body cavity.

7. The surgery supporting apparatus according to claim 1, wherein in a case where an amplitude of the sound wave signal from the receiver is not less than a predetermined threshold, the measurement device determines that the first surgical instrument is in use.

8. The surgery supporting apparatus according to claim 1, wherein the measurement device further includes a tag detection sensor attached to the first surgical instrument and configured to detect approach or contact of a tag attached to an operator, and
in a case where a plurality of surgical instruments exist and the tag detection sensor detects the tag, the measurement device determines that a surgical instrument corresponding to the tag detection sensor having detected the tag is the surgical instrument in use.

9. The surgery supporting apparatus according to claim 1, wherein the measurement device further includes an inertia sensor configured to be attached to the first surgical instrument,
and the inertia sensor measures the insertion angle of the shaft of the first surgical instrument.

10. The surgery supporting apparatus according to claim 1, wherein the measurement device measures an ultrasonic wave propagating in a space between the transmitter and the receiver.

11. The surgery supporting apparatus according to claim 1, wherein the receiver is installed in a housing detachable from the first surgical instrument.

12. The surgery supporting apparatus according to claim 1, further comprising a controller configured to output control information for controlling a posture of a second surgical instrument that is configured to be inserted into the body cavity and mechanically driven, based on the insertion depth and the insertion angle measured by the measurement device,
wherein the controller is configured to control a posture of the second surgical instrument in accordance with the control information.

13. A control method of a surgery supporting apparatus for performing a manipulation using a first surgical instrument configured to be inserted into a body cavity through a sheath tube configured to be inserted into the body cavity at an insertion position, the surgery supporting apparatus including a measurement device, the method comprising the steps of:
measuring an insertion depth and an insertion angle, with respect to the body cavity, of a shaft of the first surgical instrument with the measurement device; and
controlling a posture of a second surgical instrument that is configured to be inserted into the body cavity and mechanically driven in accordance with control information based on the insertion depth and the insertion angle measured in the measuring step,
wherein the measurement device includes a transmitter that is configured to be attached to one of the first surgical instrument and the sheath tube, and a receiver that is configured to be attached to the other of the first surgical instrument and the sheath tube, and
in the measuring step, the insertion depth is measured by measuring a sound wave propagating in a space between the transmitter and the receiver.

14. A surgery supporting system including a surgery supporting apparatus for performing a manipulation using a first surgical instrument configured to be inserted into a body cavity through a sheath tube configured to be inserted into the body cavity at an insertion position, and a medical instrument driving apparatus,
wherein the surgery supporting apparatus includes a measurement device configured to measure an insertion depth and an insertion angle, with respect to the body cavity, of a shaft of the first surgical instrument,
the measurement device includes a transmitter that is configured to be attached to one of the first surgical instrument and the sheath tube, and a receiver that is configured to be attached to the other of the first surgical instrument and the sheath tube,
the measurement device measures the insertion depth by measuring a sound wave propagating in a space between the transmitter and the receiver, and
the medical instrument driving apparatus includes a driving device configured to control a posture of a second surgical instrument that is configured to be inserted into the body cavity and mechanically driven, in accordance with control information based on the insertion depth and the insertion angle measured by the measurement device of the surgery supporting apparatus.

15. A surgery supporting apparatus for controlling a posture of a first surgical instrument that is configured to be inserted into a body cavity from a first hole in an abdominal wall and mechanically driven, by using a second surgical instrument that is configured to be inserted into the body cavity from a second hole in the abdominal wall, the apparatus comprising:
a measurement device configured to measure an insertion depth, with respect to the body cavity, of a shaft of the second surgical instrument inserted into the second hole through a sheath tube; and a controller configured to output control information for controlling the posture of the first surgical instrument, based on at least the insertion depth measured by the measurement device, wherein the controller is configured to control a posture of the first surgical instrument in accordance with the control information, the measurement device includes a transmitter that is configured to be attached to one of the sheath tube and the second surgical instrument, and a receiver that is configured to be attached to the other of the sheath tube and the second surgical instrument, and the measurement device measures the insertion depth by measuring a sound wave propagating in a space between the transmitter and the receiver.

* * * * *